US011029021B2

(12) United States Patent
Nagel

(10) Patent No.: US 11,029,021 B2
(45) Date of Patent: Jun. 8, 2021

(54) METHOD FOR OPERATING A STEAM GENERATION SYSTEM

(71) Applicant: General Electric Company, Schenectady, NY (US)

(72) Inventor: Holger Gerhard Nagel, Stuttgart (DE)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 158 days.

(21) Appl. No.: 16/161,749

(22) Filed: Oct. 16, 2018

(65) Prior Publication Data

US 2019/0120481 A1    Apr. 25, 2019

(30) Foreign Application Priority Data

Oct. 19, 2017  (EP) .................................... 17197414

(51) Int. Cl.
*F22B 35/18*     (2006.01)
*F22B 35/00*     (2006.01)
(Continued)

(52) U.S. Cl.
CPC ................ *F22B 35/00* (2013.01); *F22B 7/16* (2013.01); *F22B 35/18* (2013.01); *F22B 37/107* (2013.01); *F22B 37/38* (2013.01); *G01N 33/222* (2013.01)

(58) Field of Classification Search
CPC ...... F22B 37/38; F22B 37/42; G05B 13/0245; G05B 13/02; G05B 19/124
See application file for complete search history.

(56) References Cited

U.S. PATENT DOCUMENTS 4,969,408 A * 11/1990 Archer .................... F23N 5/006
                                                      110/347
7,398,652 B1 * 7/2008 Kosvic .................... F01K 13/02
                                                      60/664
(Continued)

FOREIGN PATENT DOCUMENTS

CN        104806995 A      7/2015
EP        3 185 203 A1     6/2017

OTHER PUBLICATIONS

Extended European Search Report and Opinion issued in connection with corresponding EP Application No. 17197414.0 dated May 11, 2018.

*Primary Examiner* — Gregory A Wilson
(74) *Attorney, Agent, or Firm* — Grogan, Tuccillo & Vanderleeden, LLP

(57) ABSTRACT

A method is disclosed for anticipating operation characteristics of a steam generation system, the steam generation system comprising at least one boiler. The method comprises conducting a fuel analysis of a solid fuel and anticipating the at least one operation characteristic of the steam generation system at the time when a specific partial quantity of solid fuel is combusted in the furnace of a boiler of the steam generation system, and further determining at least one adapted setpoint of at least one operation parameter of the steam generation system dependent upon the fuel composition of any specific solid fuel partial quantity so as to counteract and/or remedy changes of the at least one operation characteristic which are caused by the fuel composition of the specific solid fuel partial quantity. The method may be employed to improve operation of a steam generating system when the fuel composition varies.

11 Claims, 1 Drawing Sheet

(51) Int. Cl.
*G01N 33/22* (2006.01)
*F22B 7/16* (2006.01)
*F22B 37/38* (2006.01)
*F22B 37/10* (2006.01)

(56) References Cited

U.S. PATENT DOCUMENTS

| | | | |
|---|---|---|---|
| 10,185,792 B2* | 1/2019 | Cho | F22B 37/108 |
| 2004/0159270 A1 | 8/2004 | Booher | |
| 2006/0178762 A1* | 8/2006 | Wroblewski | G05B 13/027 |
| | | | 700/30 |
| 2007/0100502 A1* | 5/2007 | Rennie, Jr. | G05B 13/0275 |
| | | | 700/266 |
| 2016/0370001 A1* | 12/2016 | Sim | F23G 5/50 |

\* cited by examiner

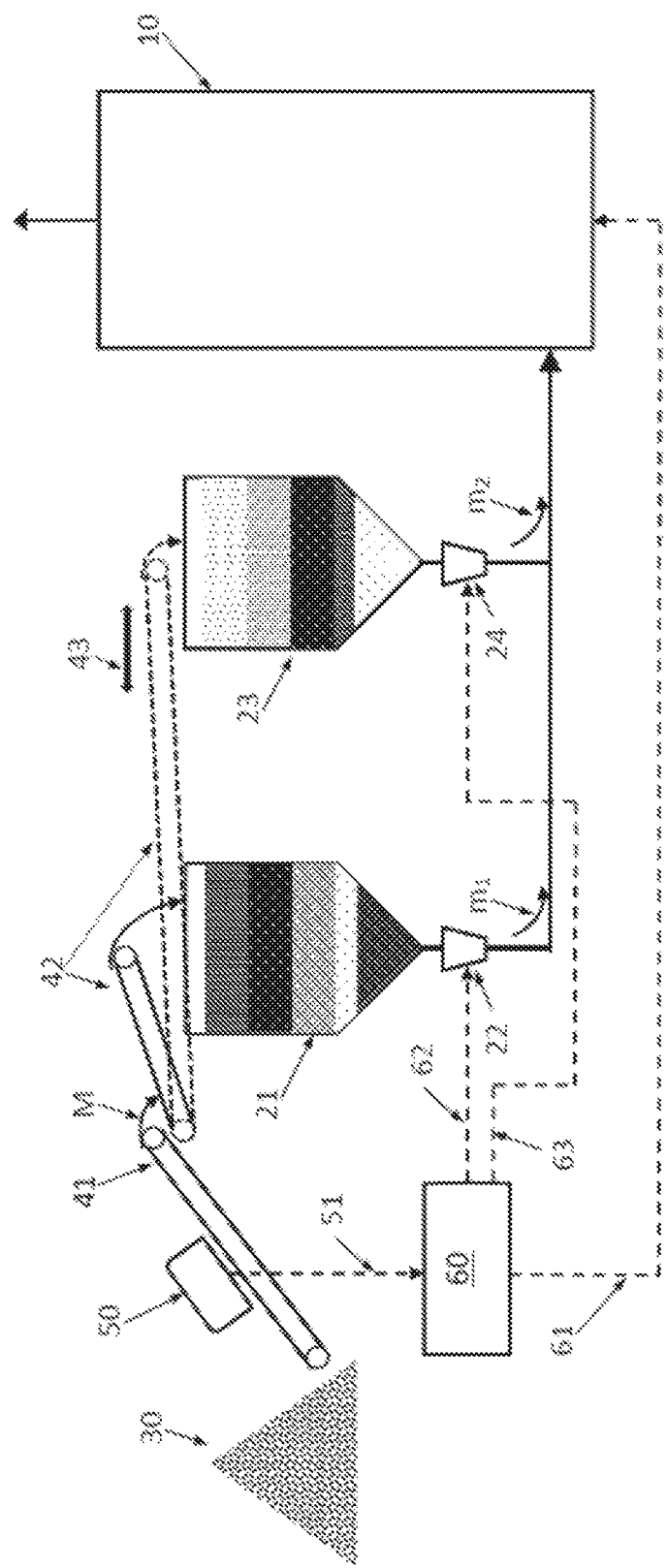

METHOD FOR OPERATING A STEAM GENERATION SYSTEM

TECHNICAL FIELD

The present disclosure relates to a method operating a steam generation system and, moreover, to a steam generation system.

BACKGROUND OF THE DISCLOSURE

Typically, solid fuel fired power generation plants, such as steam turbine power plants, have a solid fuel stock of typically several 1000 tons of solid fuel. The solid fuel stock may be referred to as the coal yard. The solid fuel typically may be coal. A fuel analysis of the fuel delivered by a supplier typically is available. The quality and composition of the fuel varies from batch to batch, dependent for instance upon the provenance of the coal. Moreover, as the fuel stock may be stored outdoors, the coal may contain a varying fracture of moisture, depending on weather conditions. Moisture, in this respect, may be understood as a content of water which is not chemically bound within the fuel and is thus able to evaporate from the fuel. The knowledge of the actual properties of the fuel combusted in the furnace of a boiler at any given time thus is, despite the available analysis of the overall batch of coal, only approximate. However, as the skilled person will readily appreciate, the actual fuel, or, in most specific instances, coal composition and contained moisture may yield a severe impact on the operation characteristics of the furnace and the boiler, but also those of the coal mills and flue gas treatment devices. Dependent upon the moisture of the coal, i.e. water physically bound water in the coal, for instance an increased water content of the coal caused by precipitation on the open coal yard, operating the mill with different drying performance may be desirable. Dependent upon the fuel composition, a different grinding fineness may be desirable. Dependent upon the ash content and composition, abrasiveness of the coal and hence mill wear may vary, as well as the slagging and fouling behaviour inside the boiler may vary. The sulfuric acid dewpoint of the flue gas may vary, and hence the allowable minimum flue gas temperature at the boiler exit, commonly after an air preheater, may vary. A specific lower heating value and other combustion characteristics of the fuel may yield a significant impact on the firing temperature distribution within the furnace, and thus, together with the Nitrogen content of the fuel, influence the formation of nitric oxides and other pollutants formed by the combustion process. This may require for instance counter action in a flue gas scrubber or a selective catalytic reactor, or SCR, or selective non-catalytic reactor, SNCR, for NOx reduction. As the skilled person will appreciate, these examples are not comprehensive.

Fuel samples may be taken from the fuel which is fed from the fuel stock to the furnace several times a day, and may be subjected to a laboratory analysis. However, due to the time delay of a laboratory analysis, the fuel is usually already consumed in the furnace before the laboratory results are available. In addition, such a procedure results in high analytic cost.

A control of operation characteristics of a solid fuel fired boiler or steam generation system based upon measured values from the furnace and the combustion gases may be found inadequate as not all significant data may be adequately available, and moreover due to the inertia of the combustion system and delay times in a control loop. It is thus found desirable to be able to anticipate changes of the fuel composition and other fuel characteristics with a sufficient lead time to be able to take adequate corrective action, if available.

OUTLINE OF THE SUBJECT MATTER OF THE PRESENT DISCLOSURE

Embodiments of the present disclosure are directed to a method and a device. In a more specific aspect, the method improves the operation of a steam generation system for different fuel compositions. The primary actions to be taken for said optimization may depend upon the focus of operation. In one aspect, it may be found desirable to influence certain operation characteristics so as to maintain them as close as possible to a target value. Generally, it may be found desirable to achieve a fair balance between the optimization of scheduled power output, for instance of a power generation plant, efficiency and related operation cost. In a more specific aspect, the method shall allow an anticipation of operation with sufficient lead time to be able to take adequate corrective action, if available.

In an embodiment, a method is disclosed for operating a steam generation system. A steam generation system is to be understood as a system comprising at least one boiler and further components, for instance provided to supply fuel to the furnace of the boiler or to treat flue gases exiting the boiler. The boiler, in turn, comprises a furnace and heat exchange surfaces. The method comprises conducting a fuel analysis of a solid fuel, so as to determine a fuel composition, that is, the relative content of certain fuel constituents, and further fuel characteristics. For instance, the lower heating value is, as will be readily appreciated, of large significance for the combustion characteristics of the fuel in a furnace of a boiler of the steam generation system. The content of volatile constituents has a large impact on the combustibility, and may as such also significantly influence the local temperature distribution and hence pollutant formation in the furnace. The sulfur content influences a minimum allowable flue gas temperature at a boiler exit and/or downstream an air preheater, so as to avoid precipitation of sulfuric acid. The total ash content is a further important parameter. The identification of specific ash constituents is significant in determining, for instance, the basicity and/or acidity of the ash and determining such characteristics as the potential for slagging of the furnace and fouling of the heat exchange surfaces above the furnace. Mineral content of the ash may have an influence on the wear of coal mills. Different moisture content of the solid fuel may also render different setpoints of certain operating parameters advisable, and/or may otherwise have an impact on the combustibility and the local temperature distribution inside the furnace. It is emphasized that this exemplary list is not necessarily comprehensive, but is only provided to facilitate understanding. The operation characteristics to be calculated may include, while not being limited to, at least one of a fouling and slagging factor, heat transfer characteristics of heating surfaces inside the boiler, a sulfuric acid dew point of the flue gas, primary nitric oxide concentration of the flue gas, and/or drying capacity of a coal mill through which the fuel is fed before being introduced into the furnace. It is understood that the operation characteristics of a steam generation system do, at least to a large extent, depend upon the fuel composition and operating parameters of the steam generation system. Thus, an action to compensate for, or remedy detrimental effect of a variation in the fuel composition may include determining at least one adapted setpoint of the respective operating parameters of the steam generation system. The setpoint may for more particular instances be adapted in response to the actual fuel composition, or the operation characteristics which are expected when combusting said fuel. The operation parameters may include, while not being limited to, the flue gas temperature at the exit of the boiler, or downstream a regenerative air preheater, respectively, which has an impact on exhaust energy losses and hence on efficiency;

the duration and/or frequency of operation of sootblowers and/or water blowers, which influence on the one hand operating cost as well as the risk for tube leakages due to immoderate blowing and on the other hand heat transfer at heat exchange surfaces and hence efficiency;

at least one of an overall air-to-fuel ratio in the furnace, local air-to-fuel ratios in the furnace, controlling thermal load distribution between different burner levels, and burner tilt angles, which influence local temperature distribution in the furnace as well as the carbon conversion and hence the formation of pollutants such as in particular nitric oxides and/or CO;

the grain size of pulverized fuel fed into the furnace; and the drying capacity of a coal mill through which the fuel is fed before being introduced into the furnace.

The method further comprises anticipating the at least one operation characteristic of the steam generation system at the time when a specific partial quantity of solid fuel is combusted in the furnace of the boiler. At least one adapted setpoint for at least one operation parameter of the steam generation system is determined so as to counteract and/or remedy changes of the at least one operation characteristic which changes are caused by the fuel composition of the specific solid fuel partial quantity. In more particular embodiments, the at least one operating parameter may be adapted dependent upon and/or responsive to the fuel composition of any specific solid fuel partial quantity, and/or the operation characteristics expected upon combustion of said solid fuel partial quantity, respectively.

The analysis of the solid fuel may be performed as an online analysis, and more in particular as a continuous analysis.

The species to be measured by the analysis may include, while not necessarily being limited to, carbon, hydrogen, sulfur, nitrogen, the moisture content, that is, the content of chemically unbound water that can be evaporated by heating the fuel, the ash content and ash constituents. Also, the ash constituents may be characterized in more detail, so as to be able to characterize the fouling and slagging characteristics.

The method thus allows an anticipation of operation characteristics of the steam generation system dependent on the composition of a partial amount of fuel before the partial amount of fuel is combusted. The method also calculates the influence of certain controllable operation parameters on the operation characteristics. As used within the framework of the present disclosure, operation parameters shall generally be understood as parameters which are under control of an operator or a control system. Operation characteristics shall be understood as values observed during and being a result of operation with a specific fuel and with the set operation parameters. The method also allows to take countermeasures against or remedies for off-design or otherwise undesired or unfavorable operation characteristics. Said countermeasures or remedies are not based upon measured values of the operation characteristics, but based upon an anticipation, and thus allows to schedule corrective and/or remedial action ahead of actual events. Some non-limiting exemplary action to be taken are outlined in more detail below and may also include for instance, while not limited to, rescheduling a plant load schedule in order not to overload a DeNOx scrubber or SCR upon combusting a nitrogen-rich fuel partial mass, change burner tilt angles and load distribution, operating sootblowers and/or water blowers to counteract slagging and fouling more frequently, and so forth. The method may in particular be suitable to improve the operation of a steam generation system or power station in term of economics, efficiency, and environmental impact.

Further effects and advantages of the disclosed subject matter whether explicitly mentioned or not, will become apparent in view of the disclosure provided below.

It is noted that within the framework of the present disclosure the use of the indefinite article "a" or "an" does in no way stipulate a singularity nor does it exclude the presence of a multitude of the named member or feature. It is thus to be read in the sense of "at least one" or "one or a multitude of".

An analysis of a specific partial fuel amount may, as will become apparent below, be performed far ahead, for instance several hours ahead, of actually combusting said specific partial amount of fuel in a furnace. The method may then comprise storing the fuel composition of the specific partial amount of fuel and determining a time when a specific partial quantity of the fuel is expected to be conveyed to a pre-combustion fuel processing device and/or the furnace of a boiler. This allows an anticipation of the operation characteristics of the steam generation system over time. If the fuel composition of each partial amount of fuel is known, e.g. in that the fuel analysis is performed continuously, a timeline of the at least one operation characteristic may be generated.

In more specific embodiments, the operation characteristic to be calculated comprises at least one of a fouling and slagging factor, heat transfer characteristics of heating surfaces inside the boiler, a sulfuric acid due point of the flue gas, primary nitric oxides concentration of the flue gas, and/or drying capacity of a coal mill through which the fuel is fed from the deployment reservoir to the furnace. A primary nitric oxides concentration is to be understood as a sum of all nitric oxides from thermally induced nitric oxides formation and from fuel bound nitrogen, in an untreated flue gas.

Said anticipated operating parameters may in certain instances be displayed to a power station operator, so that the power station operator may decide upon appropriate action to take. In other instances, a system in which the method is implemented may be configured such as to provide advice to the power station operator about possible action to take. The at least one adapted setpoint of at least one operating parameter may be displayed to the power station operator as an advice. In further exemplary embodiments a system may directly take control action and adapt the at least one operation parameter of the steam generation system to the at least one adapted operation parameter setpoint.

Accuracy may be largely enhanced in evaluating deviations between an anticipated value, a measured value and a target value of at least one operation characteristic. In particular, plausibility of the anticipated values and the measured values may be verified, and said plausibility check may be used to detect defective instrumentation and the like. The comparison may also serve to align measurements and calculations.

In most common instances, a fuel mill is provided upstream the furnace. As a general remark, in by far the most common cases, a deployment reservoir for fuel is provided which is fed from a fuel stock, such as for instance a coal yard, and serves to feed a fuel mill. A multitude of fuel deployment reservoirs and fuel mills may be provided in functional relationship with a single boiler, and in particular each deployment reservoir may be associated with a fuel mill. In said instances, the method comprises conveying the fuel to the fuel mill, grinding the fuel in the fuel mill, and conveying the fuel from the mill to the furnace of the boiler. The at least one operating parameter for which an adapted setpoint is determined may in certain embodiments comprise a mill operation parameter at the time when the partial fuel amount is processed in the mill. Said mill operating parameter may include, while not being limited to, an air supply mass flow and temperature to the mill which influences the drying capacity of the mill, and the grain size of the fuel after processing in the mill, which may be influenced, for instance, by the grinding force, the classifier speed in the mill, and the residence time of the fuel in the mill. For instance, in response to an increased fuel moisture content, and the related effect on the steam generation system operation on fuel with an increased moisture, or water content, an increased flow of drying air to the mill or a decrease in mill load may be determined as an adapted setpoint. Also, if an overall decreased combustibility of the fuel is detected, for instance due to a decreased volatiles content, this may be offset in adapting a setpoint for the grinding force so as to provide a finer ground fuel powder to the furnace. The system on which the method is performed may, under certain circumstances, issue an advice to the operator or an instruction to a plant control system to reduce fuel mass flow to a mill to prevent mill trip, i.e. emergency shutdown of the mill. Further, dependent on a content of abrasive ash constituents in the fuel, a wear factor of the mill may be calculated, which may serve, for instance, to schedule maintenance of the mill.

According to further aspects of the herein disclosed method, the at least one operating parameter for which an adapted setpoint is determined may comprise the boiler exit temperature of the flue gas, that is, the flue gas temperature downstream a last heat exchange surface of the boiler and/or a regenerative air preheater, dependent on the expected sulfuric acid dew point in the flue gas. As will be appreciated, generally a sulfuric acid precipitation should be avoided in order to prevent heavy corrosion. At a low sulfur content of the fuel, this temperature should be decreased, yielding an efficiency gain. At a comparatively higher fuel sulfur content, said temperature must be increased so as to avoid sulfuric acid precipitation.

According to still further aspects of the herein disclosed method, the at least one operating parameter for which an adapted setpoint is determined comprises the duration and/or frequency of operation of sootblowers and/or water blowers. In this respect, the method may for instance calculate fouling and slagging factors, and may consider for instance a ferric/calcium ratio, the basicity or acidity of the ash, content of iron disulfite and other ash characteristics. These allow calculating risks for slagging of the furnace and fouling of the heat exchange surfaces downstream the furnace along the flow path of the combustion gases. The duration and/or frequency of sootblower and waterblower operation is the increased in times when a fuel with comparatively higher fouling and slagging potential is combusted, so as to avoid or reduce a negative impact of fouling and slagging, which would otherwise yield a negative impact on boiler efficiency. On the other hand, in times when a fuel with comparatively lower fouling and slagging potential is combusted, the duration and/or frequency of sootblower and waterblower operation is the decreased, which yield in savings on the cost of sootblower and waterblower operation.

According to still further aspects of the herein disclosed method, the at least one operating parameter for which an adapted setpoint is determined comprises at least one of an overall air-to-fuel ratio in the furnace, a local air-to-fuel ratio in the furnace, thermal load distribution between different burner levels, and controlling burner tilt angles. Said operating parameter adaption may result in changes in the temperature distribution inside the furnace, as well as a variation of the furnace mean temperature. This has an influence on the formation of pollutants in the flue gas, namely the thermally induced formation of nitric oxides or increased carbon monoxide due to incomplete combustion, but also on the fouling and slagging potential.

Based upon an anticipation of nitric oxides formation, a schedule for the required flow of ammonia or other solvent for nitric oxides reduction in a selective catalytic reactor, also referred to as SCR, or a flue gas scrubber may be scheduled in advance. Air-to-fuel ratios may be calculated in advance for a specific partial amount of fuel to be combusted and boiler load, so as to optimize primary and secondary nitric oxide reduction measures in order to achieve acceptable levels of pollutants to be discharged to the environment at acceptable operation cost and efficiency, while at the same time achieving maximum revenue from steam generation system and/or power plant operation. Based upon an overall combustion/emission calculation, the method may comprise providing advice or taking direct control action to optimize balance between a reduction of air flow, having an impact on the auxiliary power for fan operation, and limiting maximum allowable carbon monoxide content in the flue gas and minimizing unburnt carbon. A forward calculation for changing fuel composition or load changes may serve to avoid peaks of nitric oxide formation and suboptimal combustion.

The heat transfer of the heat exchange surfaces in the boiler may be anticipated. Advice may be provided to the operator or direct control be taken to improve soot blower operation to minimize heat exchange tube erosion while at the same time preventing severe fouling. Advice or control action may be provided regarding fuel/air ratio and burner adjustment.

In response to a fuel composition yielding unfavorable fuel characteristics, such as, for instance, comparatively high ash content yielding high fouling and slagging potential, comparatively high fuel bound nitrogen content, yielding high nitric oxide emissions in adding to the emissions of thermally induced nitric oxides, or comparatively high sulfur content yielding a high sulfuric acid dew point in the flue gas, the at least one operating parameter for which an adapted setpoint is determined may comprise a mass flow ratio at which fuel from two different partial amounts of fuel is provided to the furnace of the boiler. "Comparatively high", in this respect, will be understood by the skilled person for instance as values higher than a nominal operation range specified by the operator or manufacturer, or a multiple of a nominal value specified by the operator or manufacturer. In blending a fuel with an unfavorable fuel composition with a fuel with a favorable fuel composition, the resulting fuel blend combusted in the furnace may be adjusted so as to yield species concentrations within a nominal operation range or within an acceptable tolerance band around a nominal fuel composition. In installations in which at least two deployment reservoirs for solid fuel are provided, the at least one operating parameter for which an adapted setpoint is determined may comprise the ratio of fuel mass flows from each deployment reservoir to the furnace of the boiler In other instances, the power station operator may choose to reduce thermal load of the steam generation system in times when for instance a fuel yielding an undesirable high fuel bound nitrogen content is combusted. With this measure, the generation of thermally induced nitric oxides may be reduced and/or the flue gas mass flow may be reduced such that a DeNOx device may be able to remove a sufficient amount of nitric oxide to remain within an admissible emission range for the flue gas discharged into the environment.

As noted above, a steam generation system installation and/or a power station may typically be associated with a fuel stock, for instance a coal yard, and at least one deployment reservoir associated with a furnace. A conveyor device is provided to convey fuel from the fuel stock to the at least one deployment reservoir. In common installations, two or more deployment reservoirs are associated with a furnace. The deployment reservoir or the entirety of all deployment reservoirs which are provided in a steam generation system may typically have a capacity to contain an amount of fuel sufficient for several hours of nominal full load operation of the steam generation system. The deployment reservoir or the deployment reservoirs are typically filled from top, and the content is discharged at the bottom. Thus, each partial quantity of solid fuel is associated with a solid fuel layer in a deployment reservoir. Layers of fuel deposited in a deployment reservoir generally tend to intermix only very insignificantly while passing through the deployment reservoir from top to bottom. Knowing the fuel mass flow discharged from the deployment reservoir, it can always be determined with high accuracy where in the deployment reservoir a specific partial quantity of the fuel is located, or when the specific partial quantity of the fuel is discharged from the deployment reservoir. The skilled person will readily be able to account for eventual intermixing in using models appropriately considering intermixing dependent on the specific geometry and other parameters of the deployment reservoir.

Thus, it can be calculated which specific partial quantity of the fuel is presumably discharged from the deployment reservoir at a specific time under the assumption of a specific discharge mass flow.

From the at least one deployment reservoir, fuel is fed to the furnace. A solid fuel processing device may be provided between the deployment reservoir and the furnace. The solid fuel processing device may be a coal mill. The deployment reservoirs are in this case also referred to as mill bunkers. In installations of this type the method may comprise conveying a solid fuel mass flow from a fuel stock, e.g. a coal yard, to a deployment reservoir, e.g. a mill bunker, and performing an on-line fuel analysis while conveying the fuel from the fuel stock to the deployment reservoir so as to determine fuel composition. In more specific embodiments, the fuel analysis result for specific partial amounts of fuel may be stored. The method may then further comprise calculating a time when a specific partial quantity of the fuel is expected to be discharged from the deployment reservoir to the furnace of the boiler based upon a fuel content of the deployment reservoir when the specific partial quantity of the fuel is stored into the deployment reservoir, and the mass flow of fuel discharged from the deployment reservoir. This is enabled by the fact that deployment reservoirs are commonly filled from the top and the fuel is taken from a deployment reservoir at the bottom. Each partial quantity of the fuel thus forms a horizontal layer inside the deployment reservoir. As mentioned above, the intermixing of the layers within a deployment reservoir is insignificant or is otherwise accounted for by appropriate models dependent on the bunker design and the fuel. As the skilled person will readily appreciate, a layer moves through a deployment reservoir from top to bottom as fuel is extracted at the bottom of the deployment reservoir. Thus, the position of each layer, that is, of each specific partial quantity of fuel, can be determined inside the deployment reservoir. If a schedule at which fuel is extracted from a deployment reservoir is known, the time at which a specific partial amount of the fuel is extracted from a deployment reservoir can be anticipated. It is clear in this respect, that this forecast or anticipation needs to be updated if an actual extraction schedule from a deployment reservoir deviates from a predicted extraction schedule on which the anticipation is based. The skilled person will further appreciate that a delay time may need to be considered when anticipating the combustion and/or steam generation system operation characteristics, that is, a delay time caused by conveying the fuel from the deployment reservoir and by potential processing of the fuel along that way, for instance by grinding the fuel in a mill.

If the fuel composition of each layer in a deployment reservoir is known, an anticipated timeline of the at least one operation characteristic may be generated.

The skilled person will appreciate that for determining adapted setpoints for the furnace operation parameters the time at which the fuel is actually combusted in the furnace must be considered, while for determining adapted setpoints for the mill operation parameters, for instance, the time at which the fuel is delivered to the mill must be considered. In certain instances the conveying times from the deployment device on may be neglected.

If the online analysis of the fuel is performed after the fuel has been taken from the fuel stock and before the fuel is deposited in a deployment reservoir, the operation characteristics can be anticipated up to several hours ahead of their actual occurrence, such as to provide plenty of time to schedule appropriate countermeasures, remedies, or other appropriate action.

A measurement of the coal mass flow may be performed, and is required to determine timelines if the fuel analysis is performed before the fuel is deposited in the deployment reservoir or reservoirs.

A Prompt Gamma Neutron Activation Analyzer may be employed to perform an online fuel analysis.

Further disclosed is a steam generation system comprising a boiler including a furnace, a solid fuel stock, at least one fuel deployment reservoir, and at least one conveyor device arranged for conveying solid fuel from the solid fuel stock to the at least one fuel deployment reservoir. Further, means are provided for conveying fuel from the at least one deployment reservoir to the furnace. An online fuel analyzer is provided at the conveyor device between the solid fuel stock and the at least one fuel deployment reservoir. The online fuel analyzer is provided in operative connection with a control device which is provided for controlling at least one operation parameter of the steam generation system.

In more specific embodiments of the steam generation system, the steam generation system comprises at least two fuel deployment reservoirs. The at least one conveyor device comprises, in said more specific embodiments, a first conveyor device having an upstream end and a downstream end, with respect to a conveying direction, wherein the upstream end is configured to receive fuel from the solid fuel stock. Further, the steam generation system comprises a conveyor and distribution device, wherein an upstream end of the conveyor and distribution device is arranged to receive fuel from the first conveyor device and a downstream end of the conveyor and distribution device is mobile to be placed for supplying fuel to either of the deployment reservoirs. The online fuel analyzer is provided at the first conveyor device.

It is understood that the features and embodiments disclosed above may be combined with each other. It will further be appreciated that further embodiments are conceivable within the scope of the present disclosure and the claimed subject matter which are obvious and apparent to the skilled person.

BRIEF DESCRIPTION OF THE DRAWINGS

The subject matter of the present disclosure is now to be explained in more detail by means of selected exemplary embodiments shown in the accompanying drawings. The sole FIGURE shows an exemplary embodiment of a steam generation system.

It is understood that the drawings are highly schematic, and details not required for instruction purposes may have been omitted for the ease of understanding and depiction. It is further understood that the drawings show only selected, illustrative embodiments, and embodiments not shown may still be well within the scope of the herein disclosed and/or claimed subject matter.

EXEMPLARY MODES OF CARRYING OUT THE TEACHING OF THE PRESENT DISCLOSURE

The sole FIGURE is a schematic depiction of a solid fuel fired steam generation system. A boiler 10 comprises in its interior a furnace at the bottom and heat exchange tubing above the furnace. Flue gas exits the boiler as indicated by the arrow at the top. From the flue gas exit of the boiler, the flue gas may for instance be directed to devices for removing pollutants from the flue gas, such as for instance, but not limited to, an SCR or a scrubber and an electrostatic filter for removing ash particles. The furnace of the boiler is supplied with a solid fuel from a solid fuel stock, for instance a coal yard 30. From the coal yard the coal is conveyed by a conveyor belt 41 to a reverse distribution belt or so called tripper car 42. This distal or downstream end of reverse distribution belt 42 is mobile as indicated by arrow 43. The distal or downstream end of reverse distribution belt 42 may be moved between a multitude of mill bunkers. In this specific exemplary embodiments, two mill bunkers 21 and 23 are shown. A different number of mill bunkers may be provided. The mill bunkers act as deployment reservoirs for deploying the coal for being processed in mills 22 and 24, from where ground coal is supplied to the furnace of boiler 10. The mill bunkers are alternatingly supplied with coal by reverse distribution belt 42. The entirety of the mill bunkers typically contains sufficient coal for several hours of full load operation of the furnace, or of boiler 10, respectively. Coal yard 30 holds a huge amount of coal which has been supplied by various suppliers and which commonly comprises coal of different provenance. Moreover, different partial amounts of the coal in coal yard 30 may have been exposed to rain, or, heat and sun, for different durations and at different intensity. Thus, different partial amounts of the coal in coal yard 30 may have different characteristics, for instance as to the composition and moisture content. Consequently, the fuel characteristics of the coal supplied to mill bunkers 21 and 23 may differ over time. Different partial amounts of coal with different fuel characteristics form layers of different fuel characteristics in the deployment reservoirs, or mill bunkers, respectively. Said layers are indicated by different patterns in mill bunkers 21 and 23. An online analytics device 50 is provided at conveyor belt 41. Online analytics device 50 allows a determination of solid fuel constituents while they are conveyed from coal yard 30 to mill bunkers 21 and 23. Online analytics device 50 is in operative connection with a control device 60 which is provided to control operation of the steam generation system control device 60 generates output signals representative of operation parameters of the steam generation system, and forwards the output signals to respective actuators of the steam generation system. In the exemplary embodiment, control device 60 generates at least one control signal 61 to control at least one operation parameter of boiler 10, and/or control signals 62 and 63 to control at least one operation parameter of at least one of mills 22 and 24. A measurement signal 51 from the online analytics device is transmitted to control device 60, whereby the mentioned operative connection is provided. Online analytics device 50 is in this example installed upstream, in the flow direction of the fuel, of the mill bunkers. As online analytics device 50 is installed at stationary conveyor belt 41, the installation of online analytics device 50 is significantly easier than installing it at mobile reverse distribution belt 42. As the coal is analyzed before being provided to the mill bunkers, an adaption of the operating parameters of the steam generation system may be scheduled hours ahead of actually burning a specific partial amount of fuel. On the downside, a time when a specific partial amount of fuel is actually taken from a mill bunker and is provided to the furnace must be calculated. This can be done if the mass flow M of fuel supplied to a specific mill bunker is known at any time, and furthermore the mass flows m1 and m2 from the mill bunkers to the mills, and/or from the mills to the furnace, is known. In that case, the vertical position of each layer of fuel, or each partial amount of fuel, respectively, in a mill bunker can be determined at any time. If the fuel characteristics determined by device 50 are stored for certain partial amounts of the fuel supplied to the mill bunkers, and, in more specific embodiments, for each partial amount of fuel supplied to a mill bunker, the characteristics of the fuel supplied to the furnace is known at any time. It is noted to this extent that the layers inside the mill bunkers only minimally intermix with each other. The fuel characteristics determined by device 50 are for instance stored in control device 60, and, at any time, the actual characteristics of the fuel supplied to the furnace may thus be determined in control device 60. With this knowledge, control device 60 may anticipate the operation characteristics of the steam generation system when combusting a specific partial amount of fuel under the assumption of certain settings of operating parameters of the steam generation system. With a varying fuel composition, said operation characteristics, like, for instance, the formation of nitric oxides and/or the slagging and fouling potential, will vary, and may occasionally yield undesirable and/or unfavorable values. According to the method herein disclosed, at least one adapted setpoint of at least one operating parameter of the steam generation system is determined so as to counteract and/or remedy changes of the at least one operation characteristic based upon the fuel composition of a specific solid fuel partial quantity. Said at least one adapted setpoint is, in the shown exemplary embodiment, determined by control device 60, and respective control signals 61 and/or 62 and/or 63, representative of the at least one adapted operation setpoint, are provided to respective actuators of boiler 10 and/or at least one of the mills 22 and 24.

For instance, the ash content of the fuel and the composition of ash constituents may be determined. The ash content and composition, potentially in combination with other fuel characteristics, determine the fouling and slagging behavior of the fuel, but may also have an impact on erosion inside the boiler and wear of the mills. The slagging and fouling behavior may be expressed by slagging and fouling factors. Fouling typically takes place in the upper heating surfaces, that is, the convective part, of a boiler, and describes the accumulation of ash on tubes and other exchange surfaces. Fouling is normally removed with soot blowers. Excessive fouling results in lower steam temperatures, and higher gas temperatures at the boiler outlet, and a related loss in efficiency. The flue gas path becomes constricted by the accumulation of ash, which results in increasing pressure losses, and a required higher fan power for operation of the furnace. Further, tubes can be damaged due to fouling. Large fouling chunks may damage the lower boiler parts when falling down. Slagging describes a process in which ash in a soft or molten state accumulates within the furnace and on the first heating surfaces at the furnace outlet. Slagging takes place mainly in the radiation part of the boiler where part of the ash particles are present in liquid phase. Slagging results in a decrease of heat transfer within the furnace, further yielding a decrease in the steam outlet temperature of the evaporator, with related efficiency degradation, and may further yield inhomogeneous temperature distribution of the walls and damage of the wall tubing. A specific fuel or ash can have a rather low fouling potential, but may be critical with respect to slagging, or vice versa.

The method will now be explained in more detail in describing an exemplary embodiment of dealing with coal having inhomogeneous slagging and fouling potential. As noted, the fuel composition is analyzed by analyzer 50 while the fuel, or the coal, respectively, is conveyed from coal yard 30 to one of mill bunkers 21 or 23. A mass flow M of the fuel conveyed to the respective mill bunker is further determined. This allows a determination at which vertical position in the mill bunker a specific partial amount of the fuel is deposited. With further knowledge of the mass flow from the bunker to the mill, or to the furnace, respectively, the vertical movement of a specific partial amount of fuel can be determined. Assuming a schedule of mass flow from a mill bunker to the mill, and/or to the furnace, a schedule of fuel composition fed to a mill or combusted in the furnace, respectively, can be anticipated. In a first step, the method may determine the distribution of the slagging and fouling potential of the fuel in the mill bunkers. Said distribution may be displayed to a power station operator in an analogous manner to the illustration in the drawing. The power station operator thus is informed about the slagging and fouling potential of a fuel extracted from a mill bunker and combusted in the furnace. In the exemplary embodiment shown in the drawing, for instance, a partial amount of fuel with a high slagging and fouling potential, which is beyond favorable values, is present at the bottom of mill bunker 21 and is available to be fed via mill 22 to the furnace. A partial amount of fuel with a comparatively low slagging and fouling potential is present at the bottom of mill bunker 23 and thus available to be fed via mill 24 to the furnace. Advice may be given to the plant operator to adjust mass flow m1 from mill bunker 21 and mill 22 and mass flow m2 from mill bunker 23 and mill 24 such that the resulting blend of fuel from the two mill bunkers which is actually combusted in the furnace yields a favorable or acceptably low slagging and fouling potential. In other embodiments, the method may include directly taking control action to adjust the mass flows from the bunkers accordingly. It is apparent that blending fuel from different mill bunkers, or, more generally speaking, deployment reservoirs, provides the more flexibility the more mill bunkers are associated with the boiler, or the furnace, respectively.

Further, with knowledge, or anticipation, respectively, of the slagging and fouling potential of the fuel which is actually combusted, adapted settings for the operation of soot blowers and water blowers may be determined. Soot blowers are generally operated to counteract or remove fouling, while water blowers are generally operated to counteract or remove slagging. The operation parameters for their operation may include the frequency and duration of operation. Operation of soot blowers and water blowers has a detrimental effect on the steam generation system efficiency. Furthermore, operation cost is associated with the operation of soot blowers and water blowers. With knowledge of the actual fouling and slagging potential of the actually combusted fuel, an adapted setpoint for the frequency and duration of the operation of the soot blowers and water blowers may be determined such as to achieve a reasonable trade-off between the improved heat transfer inside the boiler due to the removal of slagging and fouling, and the related efficiency gains, on the one hand, and the operation cost and efficiency loss caused by the operation of soot blowers and water blowers on the other hand.

If, for instance, the combustion of a fuel or fuel blend with an overall excessive ash content may not be avoided, a countermeasure to improve overall plant operation may be to temporarily schedule a reduced load, so as to, for instance, avoid overload of particulate filters in the exhaust treatment system of the steam generation system and related excessive particulate emissions.

Such adapted operation parameter settings may, as noted above, be displayed as an advice to an operator, but the method may also include taking direct control action in the plant control system.

For a further instance, when knowing the content of abrasive ash particles, a related wear of the fuel mills may be calculated, and with knowledge of the wear of the mills the maintenance schedule of the mills may be improved.

As becomes apparent by the description of the specific exemplary embodiment above, the herein described method allows an improvement or even optimization of plant operation in view of operation cost, plant efficiency, revenue, environmental impact of operation and so forth even with strongly varying fuel characteristics. While the method has been outlined by taking the example of ash content and related slagging and fouling characteristics, it is in the light of the explanations above apparent to the skilled person how the method may for instance be used to improve steam generation system operation for varying fuel lower heating value, nitrogen content, volatiles content, moisture and so forth.

While the subject matter of the disclosure has been explained by means of exemplary embodiments, it is understood that these are in no way intended to limit the scope of the claimed invention. It will be appreciated that the claims cover embodiments not explicitly shown or disclosed herein, and embodiments deviating from those disclosed in the exemplary modes of carrying out the teaching of the present disclosure will still be covered by the claims.

The invention claimed is:

1. A method for operating a steam generation system having at least one boiler, the method comprising:
   conducting a fuel analysis of a solid fuel and anticipating at least one operation characteristic of the steam generation system at the time when a specific partial quantity of solid fuel is combusted in the furnace of the boiler of the steam generation system; and determining at least one adapted setpoint of at least one operation parameter of the steam generation system to counteract and/or remedy changes of the at least one anticipated operation characteristic caused by the fuel composition of the specific solid fuel partial quantity, wherein the at least one operation parameter for which an adapted setpoint is determined comprises one or more of:

the boiler exit temperature of the flue gas dependent on an expected sulfuric acid dew point in the flue gas, the duration and/or frequency of operation of sootblowers and/or water blowers, at least one of an overall air-to-fuel ratio in the furnace, a local air-to-fuel ratio in the furnace, thermal load distribution between different burner levels, and/or burner tilt angles, and a mass flow (m1, m2) ratio at which fuel from two different partial amounts of fuel are provided to the furnace of the boiler.

2. The method according to claim 1, further comprising determining a time when a specific partial quantity of the solid fuel is expected to be conveyed to a pre-combustion fuel processing device and/or the furnace of the boiler of the steam generation system.

3. The method according to claim 1, wherein the at least one operation characteristic comprises at least one of a fouling and slagging factor, heat transfer characteristics of heating surfaces inside the boiler, a sulfuric acid dew point of the flue gas, and/or primary nitric oxides concentration of the flue gas.

4. The method according to claim 1, further comprising at least one of providing advice to a power station operator for improving operation characteristics of the steam generation system in adapting the steam generation system operation parameters, and/or taking direct control action to adapt the steam generation system operation parameters.

5. The method according to claim 1, further comprising evaluating deviations between an anticipated value, a measured value and a target value of at least one operation characteristic.

6. The method according to claim 1, further comprising providing a fuel mill upstream of the furnace of the boiler, conveying the fuel to the fuel mill, grinding the fuel in the fuel mill, and conveying the ground fuel from the mill to the furnace of the boiler, wherein the at least one operating parameter for which an adapted setpoint is determined comprises a mill operation parameter at the time when the partial fuel amount is processed in the mill.

7. The method according to claim 1, further comprising providing at least two deployment reservoirs for the solid fuel, wherein the at least one operation parameter for which an adapted setpoint is determined comprises the ratio of fuel mass flows (m1, m2) from each deployment reservoir to the furnace of the boiler.

8. The method according to claim 1, further comprising conveying a solid fuel mass flow from a fuel stock to a deployment reservoir and performing an on-line fuel analysis while conveying the fuel from the fuel stock to the deployment reservoir to determine the fuel composition.

9. The method according to claim 1, further comprising calculating the time when a specific partial quantity of the fuel is expected to be discharged from a deployment reservoir to the furnace of the boiler based upon a fuel content of deployment reservoir when the specific partial quantity of the fuel is stored into the deployment reservoir, and the mass flow of fuel discharged from the deployment reservoir.

10. A steam generation system, comprising:
a boiler including a furnace;
a solid fuel stock;
at least one fuel deployment reservoir;
at least one conveyor device arranged for conveying solid fuel from the solid fuel stock to the at least one fuel deployment reservoir;
means for conveying fuel from the at least one deployment reservoir to the furnace; and
an online fuel analyzer located about the at least one conveyor device between the solid fuel stock and the at least one fuel deployment reservoir, wherein the online fuel analyzer is in operative connection with a control device for controlling at least one operation parameter of the steam generation system,
wherein the at least one operation parameter comprises one or more of:
the boiler exit temperature of the flue gas dependent on an expected sulfuric acid dew point in the flue gas,
the duration and/or frequency of operation of sootblowers and/or water blowers,
at least one of an overall air-to-fuel ratio in the furnace, a local air-to-fuel ratio in the furnace, thermal load distribution between different burner levels, and/or burner tilt angles, and
a mass flow (m1, m2) ratio at which fuel from two different partial amounts of fuel are provided to the furnace of the boiler.

11. The steam generation system according to claim 10, wherein the at least one fuel deployment reservoir comprises at least two fuel deployment reservoirs, and wherein the at least one conveyor device comprises a first conveyor device having an upstream end and a downstream end, with respect to a conveying direction,
the upstream end being configured to receive fuel from the solid fuel stock via a conveyor and a distribution device, wherein an upstream end of the conveyor and the distribution device is arranged to receive fuel from the first conveyor device, and a downstream end of the conveyor and the distribution device is mobile to be placed for supplying fuel to either of the deployment reservoirs,
wherein the online fuel analyzer is provided at the first conveyor device.

* * * * *